United States Patent [19]

Crochemore et al.

[11] Patent Number: 5,686,406
[45] Date of Patent: Nov. 11, 1997

[54] VANILLIC ACID ESTER PERFUMING AGENTS

[75] Inventors: Michel Crochemore, Chaponost; Isabelle Storet, Les Eparres, both of France

[73] Assignee: Rhone-Poulenc Chimie, Courbevoie Cedex, France

[21] Appl. No.: 494,733

[22] Filed: Jun. 26, 1995

[30]    Foreign Application Priority Data

Jun. 24, 1994 [FR] France ................. 94 07811

[51] Int. Cl.$^6$ ..................................... A61K 7/46
[52] U.S. Cl. ............... 512/21; 252/174.11; 252/8.6; 424/76.4; 424/65; 424/70.1
[58] Field of Search ............. 560/67; 512/20, 512/71, 21; 252/174.11, 8.6; 424/76.4, 65, 70.1

[56]            References Cited

U.S. PATENT DOCUMENTS

| | | | |
|---|---|---|---|
| 2,580,461 | 1/1952 | Pearl | 560/67 |
| 2,644,830 | 7/1953 | Pearl | 560/67 |
| 2,650,933 | 9/1953 | Pearl | 560/67 |
| 2,675,404 | 4/1954 | Pearl | 560/67 |
| 3,729,430 | 4/1973 | Grossman et al. | 512/21 |
| 4,652,401 | 3/1987 | Schaper et al. | 512/21 |

FOREIGN PATENT DOCUMENTS 2016701   5/1970   France ................. 512/20

OTHER PUBLICATIONS

Journal of Food Science, vol. 57, No. 4, 1992 Chicago, US, pp. 985–993, 1019, R. Mriranda–Lopez et al., 'Odor analysis of Pinot Moir grapes of different maturities by a gas chromatography–olfactory technique (Osme)'.
Helvetica Chimica Acta, vol. 52, No. 1, 1969 Basel CH, pp. 24–32.
Patent Abstracts of Japan, vol. 006, No. 165 (C–121), Aug. 28, 1982 and JP-A-57 082308 (Takasago Corp.) May 22, 1982.

*Primary Examiner*—James H. Reamer
*Attorney, Agent, or Firm*—Burns, Doane, Swecker & Mathis, L.L.P.

[57]            ABSTRACT

The vanillic acid esters, for example, methyl or ethyl vanillate, are effective perfuming or olfactory agents for a wide variety of compositions, substrates and articles, whether perfumes, skin- and haircare products, cosmetics, shaving preparations, toiletries, deodorants and antiperspirants, room deodorizers, etc.

21 Claims, No Drawings

VANILLIC ACID ESTER PERFUMING AGENTS

BACKGROUND OF THE INVENTION

1. Technical Field of the Invention

The present invention relates to the perfuming of an infinite number of compositions, substrates, substances and products by formulating or incorporating therein an effective olfactory-pleasant amount of a vanillic acid ester.

This invention especially relates to perfumes, perfume compositions and perfumed products having the various scents of the vanillic acid esters.

2. Description of the Prior Art

The perfume industry, among others, is constantly seeking perfuming agents to confer unique scents to products comprised thereof, whether by reason of the originality, extent and/or strength of their fragrance.

Unfortunately, it is not possible for one skilled in this art to predict whether or not a given chemical species will have such olfactory properties or scent as to be of interest to perfume and other manufacturers.

SUMMARY OF THE INVENTION

It has now unexpectedly been determined that the vanillic acid esters exhibit original and unique olfactory properties.

Accordingly, a major object of the present invention is the provision of unique compositions, substrates, substances and products which elicit a pleasant olfactory response and which comprise at least one ester of vanillic acid.

Another object of this invention is the provision of novel perfumes, perfume compositions, perfumed substrates, substances and products that are scented with an effective amount of a vanillic acid ester.

DETAILED DESCRIPTION OF BEST MODE AND PREFERRED EMBODIMENTS OF THE INVENTION

More particularly according to the present invention, the vanillic acid ester perfuming agents advantageously have the following structural formula (I):

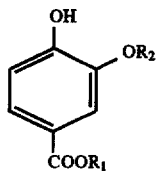

(I)

in which $R_1$ is a substituted or unsubstituted hydrocarbon radical having from 1 to 40 carbon atoms, in particular a linear or branched, saturated or unsaturated, acyclic aliphatic radical, or a saturated or unsaturated, monocyclic or polycyclic, carbocyclic or heterocyclic radical and $R_2$ is a saturated lower aliphatic radical, preferably having less than 4 carbon atoms.

In the following description of the present invention, the expression "vanillic acid" is used generically and is intended to cover both vanillic acid itself, containing a methoxy radical, as well as the higher homologs having from 2 to 4 carbon atoms in the alkoxy radical.

In the vanillic esters of formula (I), the number of carbon atoms in $R_1$ generally ranges from 1 to 40, and preferably from 1 to 12 carbon atoms.

The radical $R_1$ can be a substituted or unsubstituted monovalent radical, for example a linear or branched, saturated or unsaturated, acyclic aliphatic radical, or a monocyclic or polycyclic, saturated or unsaturated carbocyclic or heterocyclic radical.

$R_1$ is preferably a linear or branched, saturated or unsaturated acyclic aliphatic radical.

More preferably, $R_1$ is a linear or branched alkyl, alkenyl or alkadienyl radical having from 1 to 40 carbon atoms.

The hydrocarbon chain can optionally be interrupted by a heteroatom (for example oxygen or sulfur), or by one of the following groups: —CO—, —COO—, and/or bear one of the following substituents: —OH, —COOR$_3$, —X, —CF$_3$, wherein R$_3$ is preferably hydrogen or a linear or branched alkyl radical having from 1 to 4 carbon atoms, in particular a methyl or ethyl radical and X is a halogen atom.

$R_1$ can also be a monocyclic carbocyclic radical. The number of carbon atoms in the ring member can vary widely from 3 to 8 carbon atoms, but is preferably 5 or 6 carbon atoms.

The carbocycle can be saturated or contain 1 or 2 sites of unsaturation in the ring, preferably 1 or 2 double bonds.

Exemplary carbocycles are cycloalkyl or cycloalkenyl radical having from 3 to 8 carbon atoms, preferably a cyclohexyl, cyclohexenyl or cycloheptenyl radical.

When $R_1$ is a saturated or unsaturated monocyclic carbocyclic radical, one or more of the carbon atoms in the ring can be replaced by a heteroatom, preferably oxygen, nitrogen or sulfur, or by a functional group, preferably a carbonyl or ester group, to yield a monocyclic heterocyclic radical. The number of atoms in the ring member, or nucleus, can vary widely from 3 to 8, but is preferably 5 or 6 atoms.

The radical $R_1$ can also be a polycyclic carbocyclic radical, preferably a bicyclic radical, i.e., a radical wherein at least two ring members have two carbon atoms in common. In such polycyclic radicals, the number of carbon atoms in each ring preferably ranges from 3 to 6; the total number of carbon atoms is preferably 7.

Exemplary such bicyclic structures are:

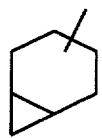

[4,1,0]

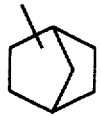

[2,2,1]

[3,1,1]

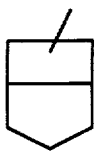

[3,2,0]

Radical $R_1$ can also be a polycyclic heterocyclic radical, preferably a bicyclic radical, i.e., a radical wherein at least two ring members have two carbon atoms in common. In this event, the number of atoms in each ring advantageously ranges from 3 to 6, preferably 5 or 6.

$R_1$ can be a linear or branched, saturated or unsaturated aliphatic radical, bearing a cyclic substituent. Exemplary cyclic substituents are cycloaliphatic, aromatic or heterocyclic substituents, in particular cycloaliphatic substituents having 6 carbon atoms in the ring, or benzene substituents. Arylalkyl radicals having 6 to 12 carbon atoms, preferably the benzyl radical, are particularly representative thereof.

It should be appreciated that if the radical $R_1$ comprises a ring member, the ring may bear any type of substituent. The typical substituents are one or more alkyl or alkoxy radicals, preferably having from 1 to 4 carbon atoms, for example three methyl radicals, a methylene radical (corresponding to an exocyclic bond), an alkenyl radical, preferably an isopropenyl radical, or a halogen atom, preferably chlorine or bromine.

More preferably, the subject vanillic acid esters have the structural formula (Ia):

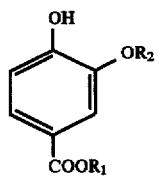

(Ia)

in which $R_1$ is a linear or branched alkyl radical having from 1 to 12 carbon atoms, preferably 1 to 6 carbon atoms, a cycloalkyl radical preferably having 6 carbon atoms or an aralkyl radical having from 6 to 12 carbon atoms, preferably 7 or 8 carbon atoms, and $R_2$ is a linear or branched alkyl radical having from 1 to 4 carbon atoms, preferably 1 or 2 carbon atoms.

The preferred compounds of formula (Ia) are those wherein $R_1$ is an alkyl radical such a methyl, ethyl, n-propyl, isopropyl, butyl, isobutyl, sec-butyl, tert-butyl, amyl, isoamyl, or n-hexyl radical, a cyclohexyl radical, or a benzyl or β-phenylethyl radical and $R_2$ is a methyl or ethyl radical.

Particularly representative vanillic acid esters of formula (Ia) include:

Methyl 4-hydroxy-3-methoxybenzoate,
Ethyl 4-hydroxy-3-methoxybenzoate,
Isopropyl 4-hydroxy-3-methoxybenzoate,
n-Propyl 4-hydroxy-3-methoxybenzoate,
n-Butyl 4-hydroxy-3-methoxybenzoate,
Amyl 4-hydroxy-3-methoxybenzoate,
Isoamyl 4-hydroxy-3-methoxybenzoate,
n-Hexyl 4-hydroxy-3-methoxybenzoate,
Cyclohexyl 4-hydroxy-3-methoxybenzoate,
Benzyl 4-hydroxy-3-methoxybenzoate,
β-Phenylethyl 4-hydroxy-3-methoxybenzoate,
Methyl 4-hydroxy-3-ethoxybenzoate,
Ethyl 4-hydroxy-3-ethoxybenzoate,
Isopropyl 4-hydroxy-3-ethoxybenzoate,
n-Propyl 4-hydroxy-3-ethoxybenzoate,
n-Butyl 4-hydroxy-3-ethoxybenzoate,
Amyl 4-hydroxy-3-ethoxybenzoate,
Isoamyl 4-hydroxy-3-ethoxybenzoate,
n-Hexyl 4-hydroxy-3-ethoxybenzoate,
Cyclohexyl 4-hydroxy-3-ethoxybenzoate,
Benzyl 4-hydroxy-3-ethoxybenzoate,
β-Phenylethyl 4-hydroxy-3-ethoxybenzoate.

The compounds of formula (I) give off a most interesting strong scent of spiced or fruity vanilla which is very different from that of vanillin.

The subject compounds can be used as perfuming ingredients in perfume compositions or substrates and in perfumed products.

By the term "perfume compositions" are intended mixtures of ingredients such as solvents, solid or liquid supports, vehicles or carriers, fixatives, various scented compounds, and the like, into which the vanillic acid esters of formula (I) are incorporated. They are used to impart the desired fragrance in various types of finished products and articles of manufacture.

Perfume bases constitute preferred examples of perfume compositions in which the vanillic acid esters of formula (I) are advantageously formulated.

Toilet waters, cosmetics, after-shave lotions, shaving preparations, perfumes, soaps, cleansing and cold creams, bath or shower gels, or deodorizing or antiperspirant products in the form of sticks or lotions, skin powders, makeups, are examples of finished substances or products to which the vanillic acid esters of formula (I) add their original note.

They can also be used in shampoos and any type of haircare and skincare products.

They are also suitable for room deodorizers, or any cleaning material.

Another example of compositions into which the subject compounds are advantageously introduced is the usual detergent compositions. These compositions generally comprise the following ingredients: anionic, cationic or amphoteric surfactants, bleaches, optical brighteners, various fillers, and antiredeposition agents. The nature of these components is not critical and the vanillic acid esters of formula (I) can be added to any type of detergent composition. They can be introduced into fabric softeners, usually nonwoven, for use in dryers.

The amount of vanillic acid ester of formula (I) in the compositions of the invention, expressed as the percentage by weight in the composition, depends on the nature of the composition (a perfume base or a toilet water, for example) and the strength and nature of the desired effect in the final product. The amount of vanillic acid ester of formula (I) in a perfume base could, of course, be very high, for example more than 50% by weight and even 90% by weight, while in a perfume, toilet water or after-shave lotion, this concentration could be much less than 50% by weight.

The amount of vanillic acid ester in detergent compositions, in particular in household detergents or soaps, is on the order of 1% to 2%.

It can also be incorporated into perfumed shampoos or any other haircare product, in the amount of 0.5% to 2%.

The lower limit for the amount of vanillic acid ester of formula (I), then, is that which perceptibly modifies the scent of the fragrance or odor of the final product. In certain instances, this minimum amount is on the order of 0.01% by weight. Amounts not within the ranges indicated above could also be used without departing from the scope of the present invention.

One process for the preparation of the subject vanillic acid esters comprises reacting vanillic acid with an alcohol, in the presence of an acidic catalyst.

More particularly, a vanillic acid of formula (II):

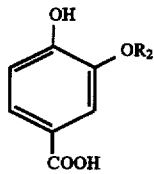
(II)

wherein $R_2$ is as defined above, is reacted with an aliphatic alcohol of formula (III):

wherein $R_1$ is also as defined above.

Vanillic acid, or 4-hydroxy-3-ethoxybenzoic acid, is particularly suitable from among the compounds of formula (II).

The preferred alcohols of formula (II) are primary alcohols having from 1 to 6 carbon atoms, more preferably methanol, ethanol or cyclohexanol.

In accordance with the process of the invention, the vanillic acid is reacted with the alcohol of formula (III).

Compounds of formula (II) are commercially available.

A number of techniques for the preparation thereof exist in this art.

In a first embodiment, vanillic acid is reacted with the alcohol of formula (III). This preparative technique is especially suitable when the alcohol used for the esterification reaction forms an azeotrope with water, permitting its elimination by azeotropic distillation.

Esterification can also be carried out in the presence of an organic solvent. The organic solvent is selected such that it forms an azeotrope with water and that the boiling point of the azeotrope with water is lower than that of the alcohol employed. Particularly exemplary solvents include toluene, cumene and pseudocumene.

Preferably, when the alcohol has from 1 to 3 carbon atoms, a direct esterification is carried out in the absence of an organic solvent.

For higher alcohols having at least 4 carbon atoms, the reaction is preferably carried out in the presence of an organic solvent.

The reactions are carried out in the presence of a conventional acidic catalyst. Particularly exemplary acid catalysts include sulfuric acid, p-toluene sulfonic acid, alkyl titanates, preferably isopropyl or n-butyl titanate, and antimony oxide.

The amount of reactants used is determined such that the alcohol of formula (III) is generally in excess with respect to the vanillic acid. The excess varies widely, preferably from 50% to 500% relative to the stoichiometric amount. It most preferably ranges from 100% to 200% of the stoichiometric amount.

The amount of catalyst used advantageously ranges from 1% to 5% relative to the weight of the vanillic acid.

When an organic solvent is present, the amount thereof can vary widely. For example, the solvent can range from 50% to 200% of the weight of vanillic acid used.

The reaction temperature is selected to be sufficient for the reaction to continue to completion.

The reaction temperature preferably ranges from 50° C. to 150° C.

The reaction is advantageously carried out at atmospheric pressure.

The reaction is preferably carried out in an inert gas atmosphere, which may be nitrogen or a noble gas, preferably argon.

The process of the invention is quite simple to carry out.

The different reactants can be introduced in any order. Preferably, the following order is observed: the vanillic acid is introduced along with the alcohol of formula (III), followed by the acidic catalyst.

The reaction medium is heated to the desired temperature, maintaining the reaction mixture stirred.

During the reaction, water forms in the reaction medium. In a preferred embodiment of the invention, the water is eliminated from the reaction medium as it is formed via any known means, in particular by azeotropic distillation.

At the end of the reaction, the desired vanillic acid ester is obtained, along with the excess alcohol of formula (III) and the catalyst.

The vanillic acid ester can be recovered from the reaction medium via any known means.

In particular, the medium can be washed with water, then neutralized with a base.

The amount of base, preferably sodium hydroxide, carbonate or bicarbonate, is such that the pH ranges from 6 to 8.

The organic phase is separated and fractionated by distillation. Typically, the excess alcohol of formula (III) is recovered first, followed by the vanillic acid ester of formula (I).

In order to further illustrate the present invention and the advantages thereof, the following specific examples are given, it being understood that same are intended only as illustrative and in nowise limitative.

EXAMPLE 1

Preparation of methyl 4-hydroxy-3-methoxybenzoate (methyl vanillate)

50 g of vanillic acid and 250 ml of methanol were introduced into a reactor provided with a magnetic stirrer, a coolant and a thermometer. 40 ml of 96% concentrated sulfuric acid was introduced dropwise using a dropping funnel; cooling was carried out if the alcohol boiled.

The mixture was refluxed for 2 hours with stirring.

The mixture was cooled to room temperature, poured into 100 ml of ice water, and the alcohol was evaporated off under reduced pressure (200 mm of mercury=$2.6 \times 10^4$ Pa).

The aqueous phase was extracted three times with ethyl ether.

The combined organic phases were washed with a saturated solution of sodium bicarbonate until the pH was neutral, then washed once with water to eliminate the salts.

The organic phase was dried over magnesium sulfate and evaporated under reduced pressure (200 mm of mercury= $2.6 \times 104$ Pa) to obtain the crude ester.

The methyl ester was distilled at 118° C. under a reduced pressure of 2 mm of mercury (266 PA), then crystallized from petroleum ether (80°–120° C. fraction) to provide methyl vanillate having a purity of more than 97% in a yield of 82%.

The methyl vanillate has a spicy vanilla scent, different than vanillin.

EXAMPLE 2

Preparation of ethyl 4-hydroxy-3-methoxybenzoate (ethyl vanillate)

50 g of vanillic acid and 250 ml of methanol were introduced into a reactor. 40 ml of sulfuric acid was introduced dropwise using a dropping funnel; cooling was carried out if the alcohol boiled.

The mixture was refluxed for 2 hours with stirring.

The mixture was cooled to room temperature, poured into 100 ml of ice water, and the alcohol was evaporated off under reduced pressure.

The aqueous phase was extracted three times with ethyl ether.

The combined organic phases were washed with a saturated solution of sodium bicarbonate until the pH was neutral, then washed once with water to eliminate the salts.

The organic phase was dried over magnesium sulfate and evaporated under reduced pressure (200 mm of mercury= 2.6600 Pa) to obtain the crude ester.

The ethyl ester was distilled at 132° C. under a reduced pressure of 2 mm of mercury (266 PA), then crystallized from petroleum ether (40°–60° C. fraction) to provide ethyl vanillate having a purity of more than 97% at a yield of 80%.

The ethyl vanillate has a spicy vanilla scent.

EXAMPLE 3

Preparation of n-hexyl 4-hydroxy-3-methoxybenzoate (n-hexyl vanillate)

59 g of vanillic acid (0.35 mole) and 41 g of dry n-hexanol (0.40) mole were added to 150 ml of toluene in a reactor equipped with a Dean-Stark condenser. 5% of p-toluene sulfonic acid was added as the acidic catalyst.

The mixture was refluxed for 24 hours, during which the elimination of water was observed.

After cooling to room temperature, the organic phase was washed with a saturated sodium bicarbonate solution until the pH was neutral.

The organic phase was then washed with water before drying over magnesium sulfate. The toluene and a portion of the n-hexanol were evaporated off under reduced pressure.

The crude ester was distilled twice at 130° C. under a reduced pressure of 2 mm of mercury (266 Pa) to provide n-hexyl vanillate having a purity of more than 97% at a yield of 57%.

The n-hexyl vanillate had a fruity vanilla scent.

EXAMPLES 4 and 5

Preparation of isopropyl 4-hydroxy-3-methoxybenzoate isopropyl vanillate)

Gaseous hydrochloric acid was bubbled into 250 g of isopropanol in a 500 ml reactor to produce a solution of 2% by weight hydrochloric acid. Since the dissolution was exothermic, the reactor was cooled in an ice bath.

25 g of vanillic acid were then added and the mixture was refluxed.

When the reaction was complete, the alcohol was distilled off and the residue was then taken up in a saturated aqueous sodium bicarbonate solution. The aqueous phase was extracted three times with ethyl ether.

The combined organic phases were washed once with water to eliminate the salts.

The organic phase was dried over magnesium sulfate and vacuum evaporated to obtain the crude ester.

The isopropyl ester was recrystallized twice from petroleum ether (80°–120° C. fraction) to provide isopropyl vanillate having a purity of more than 99% and in a yield of 77%.

The isopropyl vanillate has a slight vanilla scent. The same scent was obtained with benzyl vanillate, prepared by repeating the above procedure (Example 4), but using benzyl alcohol (Example 5).

EXAMPLE 6

Preparation of isoamyl 4-hydroxy-3-methoxybenzoate (isoamyl vanillate)

Gaseous hydrochloric acid was bubbled into 250 g of isopentanol in a 500 ml reactor to produce a solution of 2% by weight hydrochloric acid. Since the dissolution was exothermic, the reactor was cooled in an ice bath. 25 g of vanillic acid were then added and the mixture was refluxed.

When the reaction was complete, the alcohol was distilled off and the residue was then taken up in a saturated aqueous sodium bicarbonate solution.

The aqueous phase was extracted three times with ethyl ether.

The combined organic phases were washed once with water to eliminate the salts.

The organic phase was dried over magnesium sulfate and vacuum evaporated to obtain the crude ester.

The isoamyl ester was distilled under reduced pressure [148°–150° C., 2 mm of mercury (266 Pa)], then recrystallized from hexane to provide isopropyl vanillate having a purity of more than 98% and in a yield of 69%.

The isoamyl vanillate had a carnation-flower scent.

EXAMPLE 7

Cyclohexyl 4-hydroxy-3-methoxybenzoate was prepared according to the procedure of the previous example The cyclohexyl vanillate had a vanilla-olive scent.

EXAMPLE 8

The following is an example of the formulation of methyl vanillate into a liquid perfume composition.

50% $C_{11}$ Undecyclenic aldehyde (10% solution)

5% $C_{12}$ Lauric aldehyde (10% solution)

5% $C_{12}$ Methylnonylacetic aldehyde (10% solution)

180% Synthetic bergamot

50% Aurantiol® 50% diethylphthalate solution) [N-methyl-3,7-dimethyl-7-hydroxyoctylidene anthranilate]

40% Benzyl salicylate

90% Synthetic jasmine

80% Hédione (methyl dihydrojasmonate)

80% Lyral® [4-(4-hydroxy-4-methylpentyl)-3-cyclohexene-1-carboxaldehyde]

15% Eugenol

5% Isoeugenol

80% Phenylethyl alcohol

60% Methylionone

80% Vertofix® [cedr-8-enylmethyl ketone]

60% Singapore patchouli "deironed"

20% Coumarin

80% Methyl vanillate

50% Moskéne® [4,6-dinitro-1,1,3,3,5-pentamethyl indane]

A spicy perfume was obtained.

EXAMPLES 9-14

A number of compounds having the following formula were prepared:

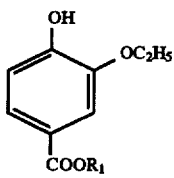

in which the radical $R_1$ is defined in the Table below.

An olfactory description of the products obtained is also reported in the Table:

TABLE

| Example | Nature of radical $R_1$ | Olfactory description |
|---------|------------------------|----------------------|
| 9       | methyl                 | carnation            |
| 10      | ethyl                  | spicy-smoky          |
| 11      | isopropyl              | metallic-vanilla     |
| 12      | n-butyl                | olive                |
| 13      | propyl                 | ethereal-wet cardboard |
| 14      | n-hexyl                | wet cardboard-olive  |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. In a scented composition of matter/product containing an olfactory effective amount of a perfuming agent, the improvement which comprises, as the perfuming agent therefor, a vanillic acid ester.

2. The composition/product as defined by claim 1, said vanillic acid ester having the structural formula (I):

(I)

in which $R_1$ is a substituted or unsubstituted hydrocarbon containing radical having from 1 to 40 carbon atoms and $R_2$ is a saturated lower aliphatic radical.

3. The composition/product as defined by claim 2, wherein formula (I), $R_1$ is a linear or branched, saturated or unsaturated, acyclic aliphatic radical, or a saturated or unsaturated, monocyclic or polycyclic, carbocyclic or heterocyclic radical.

4. The composition/product as defined by claim 3, wherein formula (I), $R_2$ has less than 4 carbon atoms.

5. The composition/product as defined by claim 2, wherein formula (I), $R_1$ has from 1 to 12 carbon atoms.

6. The composition/product as defined by claim 2, wherein formula (I), $R_1$ is a linear or branched alkyl, alkenyl or alkadienyl radical.

7. The composition/product as defined by claim 2, wherein formula (I), $R_1$ is a saturated or unsaturated monocyclic carbocyclic radical having from 3 to 8 carbon atoms.

8. The composition/product as defined by claim 2, wherein formula (I), $R_1$ is a saturated or unsaturated monocyclic heterocyclic radical having from 3 to 8 ring atoms.

9. The composition/product as defined by claim 2, wherein formula (I), $R_1$ is a polycyclic carbocyclic radical, each ring member of which having from 3 to 6 carbon atoms.

10. The composition/product as defined by claim 2, wherein formula (I), $R_1$ is a polycyclic heterocyclic radical, each ring member of which having from 3 to 6 ring atoms.

11. The composition/product as defined by claim 1, said vanillic acid ester having the structural formula (Ia):

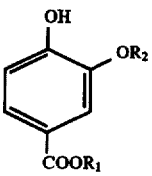

(Ia)

in which $R_1$ is a linear or branched alkyl radical having from 1 to 12 carbon atoms, a cycloalkyl radical having from 3 to 8 carbon atoms, or an aralkyl radical having from 6 to 12 carbon atoms, and $R_2$ is a linear or branched alkyl radical having from 1 to 4 carbon atoms.

12. The composition/product as defined by claim 11, wherein formula (Ia), $R_1$ is a methyl, ethyl, n-propyl, isopropyl, butyl, isobutyl, sec-butyl, tert-butyl, amyl, isoamyl, or n-hexyl radical, a cyclohexyl radical, or a benzyl or β-phenylethyl radical and $R_2$ is a methyl or ethyl radical.

13. The composition/product as defined by claim 1, said vanillic acid ester comprising methyl 4-hydroxy-3-methoxybenzoate, ethyl 4-hydroxy-3-methoxybenzoate, isopropyl 4-hydroxy-3-methoxybenzoate, n-propyl 4-hydroxy-3-methoxybenzoate, n-butyl 4-hydroxy-3-methoxybenzoate, amyl 4-hydroxy-3-methoxybenzoate, isoamyl 4-hydroxy-3-methoxybenzoate, n-hexyl 4-hydroxy-3-methoxybenzoate, cyclohexyl 4-hydroxy-3-methoxybenzoate, benzyl 4-hydroxy-3-methoxybenzoate, β-phenylethyl 4-hydroxy-3-methoxybenzoate, methyl 4-hydroxy-3-ethoxybenzoate, ethyl 4-hydroxy-3-ethoxybenzoate, isopropyl 4-hydroxy-3-ethoxybenzoate, n-propyl 4-hydroxy-3-ethoxybenzoate, n-butyl 4-hydroxy-3-ethoxybenzoate, amyl 4-hydroxy-3-ethoxybenzoate, isoamyl 4-hydroxy-3-ethoxybenzoate, n-hexyl 4-hydroxy-3-ethoxybenzoate, cyclohexyl 4-hydroxy-3-ethoxybenzoate, benzyl 4-hydroxy-3-ethoxybenzoate, or β-phenylethyl 4-hydroxy-3-ethoxybenzoate.

14. The composition/product as defined by claim 1, comprising a perfume or perfume base.

15. The composition/product as defined by claim 1, comprising a deodorant or antiperspirant.

16. The composition/product as defined by claim 1, comprising a skincare or haircare formulation.

17. The composition/product as defined by claim 1, comprising a detergent or cleansing composition.

18. The composition/product as defined by claim 1, comprising a toiletry, cosmetic or makeup.

19. The composition/product as defined by claim 1, comprising a bath or shower composition.

20. The composition/product as defined by claim 1, comprising a room deodorizer.

21. The composition/product as defined by claim 1, comprising a fabric softener.

* * * * *